United States Patent
Pai et al.

(10) Patent No.: US 7,643,124 B2
(45) Date of Patent: Jan. 5, 2010

(54) LIQUID CRYSTAL, AND LIQUID CRYSTAL MATERIAL COMBINATION AND LIQUID CRYSTAL DISPLAY EACH CONTAINING THE SAME

(75) Inventors: Chia-Hsuan Pai, Hsinchu (TW); Chao-Yuan Chen, Hsinchu (TW); Te-Sheng Chen, Hsinchu (TW); Jenn-Jia Su, Hsinchu (TW)

(73) Assignee: AU Optronics Corp., Hsinchu (TW)

( * ) Notice: Subject to any disclaimer, the term of this patent is extended or adjusted under 35 U.S.C. 154(b) by 185 days.

(21) Appl. No.: 12/018,522

(22) Filed: Jan. 23, 2008

(65) Prior Publication Data
US 2009/0086139 A1    Apr. 2, 2009

(30) Foreign Application Priority Data
Sep. 28, 2007    (TW) ............... 96136237 A

(51) Int. Cl.
*C09K 19/02*    (2006.01)
(52) U.S. Cl. .............. 349/167; 349/168; 349/169; 349/170; 349/180; 349/182
(58) Field of Classification Search .......... 349/168–170
See application file for complete search history.

(56) References Cited

U.S. PATENT DOCUMENTS

| | | | |
|---|---|---|---|
| 5,668,651 | A | 9/1997 | Yamada et al. |
| 2003/0048401 | A1 | 3/2003 | Hanaoka et al. |
| 2005/0146664 | A1 | 7/2005 | Hanaoka et al. |
| 2006/0198968 | A1 | 9/2006 | Goto et al. |

FOREIGN PATENT DOCUMENTS

| | | |
|---|---|---|
| CN | 1117142 | 2/1996 |
| JP | 2006-18116 | 1/2006 |
| JP | 2006133619 | 5/2006 |
| TW | 200528539 | 3/2005 |

OTHER PUBLICATIONS

English language translation of abstract of TW 200528539.
English language translation of abstract of JP 2006133619.
Chinese language office action dated May 8, 2009.
English language translation of abstract and pertinent parts of JP 2006-18116.

*Primary Examiner*—David Nelms
*Assistant Examiner*—Phu Vu
(74) *Attorney, Agent, or Firm*—Thomas, Kayden, Horsetemeyer & Risley

(57) ABSTRACT

A liquid crystal is provided, which can be used in a liquid crystal display (LCD) to provide an LCD exhibiting a good transmittance. The liquid crystal according to the invention has the following properties:
 (i) a dielectric anisotropy ($\Delta\in$) ranging from about −2.5 to about −5;
 (ii) a splay elastic constant ($K_{11}$) ranging from about $1.1\times 10^{-11}$ N to about $1.6\times 10^{-11}$ N;
 (iii) a bend elastic constant ($K_{33}$) ranging from about $1.1\times 10^{-11}$ N to about $1.6\times 10^{-11}$ N; and
 (iv) $\Delta\in$, $K_{11}$ (N) and $K_{33}$ (N) conforming to the following equation:

$$\frac{K_{11}+K_{33}}{|10\times\Delta\varepsilon|} < 1.28\times 10^{-12}.$$

A liquid crystal material combination is also provided which comprises the liquid crystal according to the invention above mentioned and a polymerizable monomer.

23 Claims, 2 Drawing Sheets

LIQUID CRYSTAL, AND LIQUID CRYSTAL MATERIAL COMBINATION AND LIQUID CRYSTAL DISPLAY EACH CONTAINING THE SAME

CROSS-REFERENCES TO RELATED APPLICATIONS

BACKGROUND OF THE INVENTION

1. Field of the Invention

The present invention relates to a liquid crystal for use in a liquid crystal display (LCD); and more particularly, relates to a liquid crystal material combination for use in a polymer sustained alignment (PSA) LCD.

2. Descriptions of the Related Art

In the display apparatus market, LCDs are the most established and popular displays. The LCDs have many advantages over the conventional cathode ray tube (CRT) display, such as a light weight, low power consumption, good portability and radiation-free. Therefore, the LCD has been widely used in 3C products such as mobile phones, digital cameras, notebook computers and desktop displays.

The property of the liquid crystal material has a critical impact on the performance of the LCD. Generally, in terms of dielectric anisotropy ($\Delta\in$), the liquid crystal material may be classified into a positive type liquid crystal material (i.e., $\Delta\in>0$) and a negative type liquid crystal material ($\Delta\in<0$). The positive type liquid crystal material is typically used in a parallel alignment (PA) LCD, while the negative type liquid crystal material is typically used in a vertical alignment (VA) LCD.

To improve the performance of the LCD, technologies of assisted liquid crystal alignment have been proposed to provide liquid crystal molecules with a pretilt angle, in an attempt to obtain an LCD featuring a fast response and a high contrast ratio. One of the assisted alignment technologies is to add a polymerizable monomer into the liquid crystal material. Once polymerized, the polymerized monomer gives the liquid crystal molecules a pretilt angle, thus achieving an assisted alignment effect and an improved optical behavior. An LCD using such a liquid crystal material doped with a polymerizable monomer is commonly known as a polymer sustained alignment (PSA) LCD.

However, since the pixel structures of LCDs have become increasingly complicated, and particularly with the development of the multi-domain pixel structure, the LCD industry is facing a challenge of coping with the decreasing liquid crystal transmittance. Briefly speaking, the effective electrical field has become increasingly smaller given the same driving voltage. Consequently, with other conditions kept the same, transmittance of the liquid crystal material will tend to decrease, thus imposing an adverse impact on the optical behavior of the LCDs.

In view of the above problem, the inventors of the present application have found in a research that, by selecting a liquid crystal material having particular characteristics, the optical performance, e.g., the transmittance, of the LCD can be improved.

SUMMARY OF THE INVENTION

One objective of this invention is to provide a liquid crystal display, comprising:
a first substrate;
a second substrate; and
a plurality of liquid crystal molecules sealed between the first substrate and the second substrate, having following properties:
(i) a dielectric anisotropy ($\Delta\in$) ranging from about −2.5 to about −5;
(ii) a splay elastic constant ($K_{11}$) ranging from about $1.1\times 10^{-11}$ N to about $1.6\times 10^{-11}$ N;
(iii) a bend elastic constant ($K_{33}$) ranging from about $1.1\times 10^{-11}$ N to about $1.6\times 10^{-11}$ N; and
(iv) a relationship among $\Delta\in$, $K_{11}$(N) and $K_{33}$(N) being as follows:

$$\frac{K_{11}+K_{33}}{|10\times\Delta\varepsilon|} < 1.28\times 10^{-12}.$$

Another objective of this invention is to provide a liquid crystal having following properties:
(i) a dielectric anisotropy ($\Delta\in$) ranging from about −2.5 to about −5;
(ii) a splay elastic constant ($K_{11}$) ranging from about $1.1\times 10^{-11}$ N to about $1.6\times 10^{11}$ N;
(iii) a bend elastic constant ($K_{33}$) ranging from about $1.1\times 10^{-11}$ N to about $1.6\times 10^{-11}$ N; and
(iv) a relationship among $\Delta\in$, $K_{11}$(N) and $K_{33}$(N) being as follows:

$$\frac{K_{11}+K_{33}}{|10\times\Delta\varepsilon|} < 1.28\times 10^{-12}.$$

Still another objective of this invention is to provide a liquid crystal material combination, comprising a plurality of liquid crystal molecules as described above and a polymerizable monomer.

With reference to the figures and the method described below, people skilled in the field of the invention can easily realize the basic spirit and other objectives of the subject invention and the technical means and preferred embodiments used thereby.

DESCRIPTION OF THE PREFERRED EMBODIMENT

Figure 1:
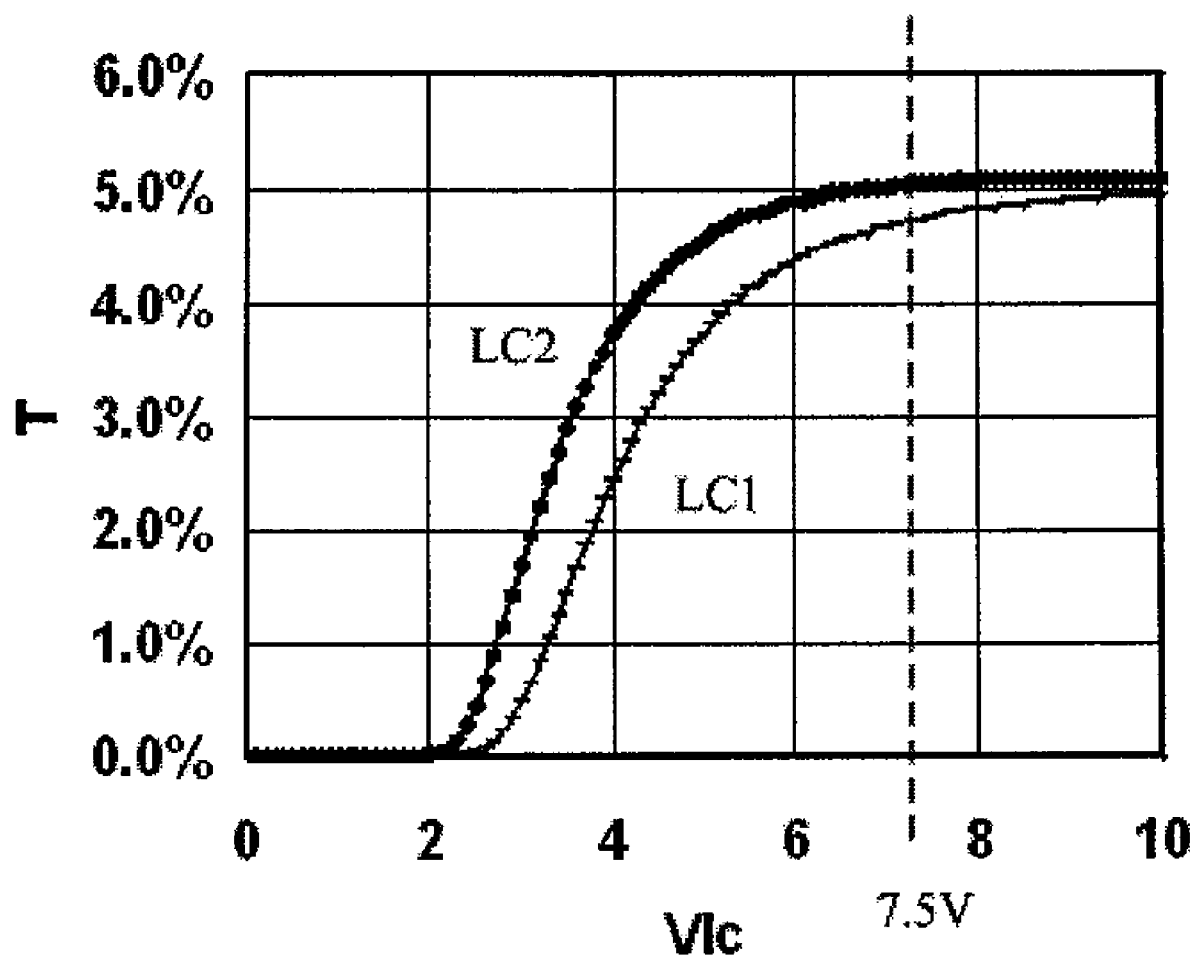
FIG. 1 depicts a graph comparing the transmittance variations as a function of the driving voltage when changing the liquid crystal parameters in an identical LCD structure.

Research has shown that once the driving voltage is increased to a certain extent (around 10 V), transmittance of the liquid crystal material will become saturated irrespective of the parameters thereof. However, due to the practical limitations in the current display panels, the driving voltage adopted is usually inadequate to render a saturated transmittance. The above phenomenon can be explained in detail by a graph of the transmittance versus the driving voltage as shown in FIG. 1. Two kinds of liquid crystal material with different $K_{11}$, $K_{33}$ and $\Delta\in$, i.e. a liquid crystal material LC1 ($K_{11}=K_{33}=1.33\times 10^{-11}$ N, $\Delta\in=-3.5$) and a liquid crystal material LC2 ($K_{11}=K_{33}=1.33\times 10^{-11}$ N, $\Delta\in=-3.1$) were tested respectively with the same pixel structure using the same measurement method. It turned out that the transmittance increase, as a function of the voltage, was quite different for the two kinds of liquid crystal materials. For example, under a commonly used driving voltage of 7.5 V, LC2 demonstrated a higher transmittance than LC1. Further research has also revealed that given the same driving voltage, $K_{11}$, $K_{33}$ and $\Delta\in$ of a liquid crystal material are the key factors that impact the transmittance thereof.

Therefore, this invention provides a liquid crystal with specific properties. In particular, the parameters $K_{11}$, $K_{33}$ and $\Delta\in$ of the liquid crystal conform to the following conditions:
(i) $\Delta\in$ ranges from about −2.5 to about −5;
(ii) $K_{11}$ ranges from about $1.1\times10^{-11}$ N to about $1.6\times10^{-11}$ N;
(iii) $K_{33}$ ranges from about $1.1\times10^{-11}$ N to about $1.6\times10^{-11}$ N; and
(iv) a relationship among $\Delta\in$, $K_{11}$(N) and $K_{33}$ (N) is as follows:

$$\frac{K_{11}+K_{33}}{|10\times\Delta\varepsilon|} < 1.28\times10^{-12}.$$

According to this invention, any liquid crystal with the above properties may be used in an LCD to provide an adequate transmittance, and is not subjected to any specific limitation. For example (but not limited to), the liquid crystal of this invention may be selected from a group consisting of compounds with a formula (III), (IV), (V) or (VI):

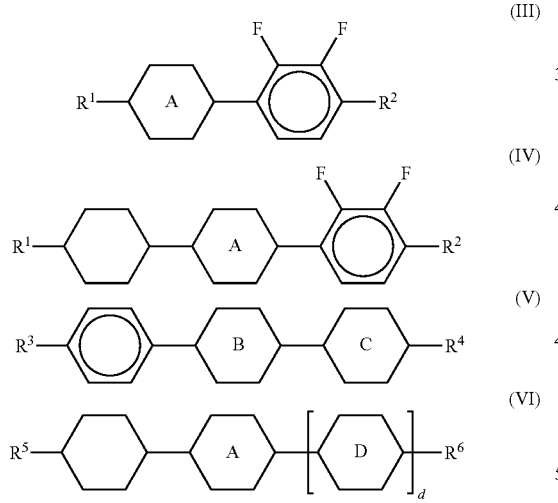

wherein,
$R^1$, $R^2$, $R^3$, $R^4$ and $R^6$ are independently alkyl with 1 to 12 carbon atoms, wherein one $CH_2$ group or two $CH_2$ groups that are not adjacent to each other can be replaced by —O—, —CH=CH—, —CO—, —OCO— or —COO—;
$R^5$ is alkenyl with 2 to 8 carbon atoms;
d is 0 or 1;

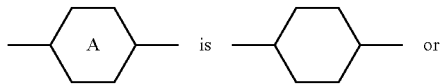

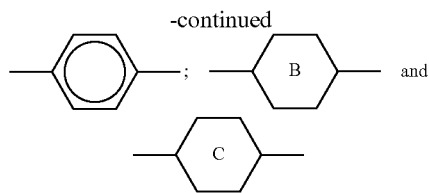

and are independently

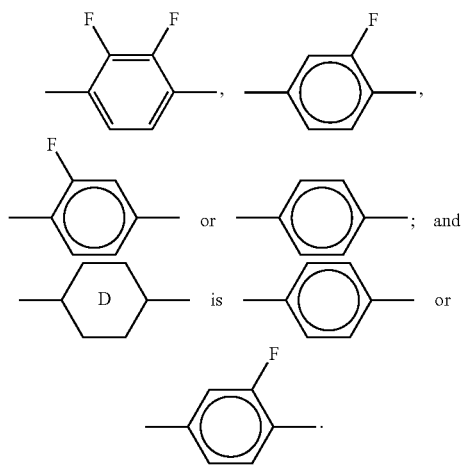

In a preferred embodiment of the liquid crystal of this invention, the parameters $K_{11}$, $K_{33}$ and $\Delta\in$ adopted are as follows:
(i) $\Delta\in$ ranges from about −3 to about −5;
(ii) $K_{11}$ ranges from about $1.1\times10^{-11}$ N to about $1.6\times10^{-11}$ N;
(iii) $K_{33}$ ranges from about $1.1\times10^{-11}$ N to about $1.6\times10^{-11}$ N; and
(iv) a relationship among $\Delta\in$, $K_{11}$ (N) and $K_{33}$ (N) is as follows:

$$\frac{K_{11}+K_{33}}{|10\times\Delta\varepsilon|} < 1.28\times10^{-12}.$$

In another preferred embodiment of the liquid crystal of this invention, the parameters $K_{11}$, $K_{33}$ and $\Delta\in$ adopted are as follows:
(i) $\Delta\in$ ranges from about −3 to about −5;
(ii) $K_{11}$ ranges from about $1.37\times10^{-11}$ N to about $1.6\times^{-11}$ N;
(iii) $K_{33}$ ranges from about $1.37\times10^{-11}$ N to about $1.6\times10^{-11}$ N; and
(iv) a relationship among $\Delta\in$, $K_{11}$(N) and $K_{33}$(N) is as follows:

$$\frac{K_{11}+K_{33}}{|10\times\Delta\varepsilon|} < 1.28\times10^{-12}.$$

As described above, by selecting a liquid crystal with a particular combination of parameters ($\Delta\in$, $K_{11}$, and $K_{33}$), this invention provides a suitable liquid crystal. When the liquid crystal is used in an LCD, the optical performance of the LCD is improved.

This invention thus also provides an LCD and particularly a PSA LCD. The LCD according to the invention comprises a first substrate, a second substrate, and the liquid crystal according to the invention sealed therebetween. Also, a first electrode and a second electrode are respectively disposed on the surfaces of the first substrate and the second substrate. Optionally, an alignment film (e.g., polyimide) can be disposed on the first electrode and/or the second electrode.

For a PSA LCD, it further comprises a polymer film disposed on the alignment film, wherein the polymer film is polymerized from a polymerizable monomer. The polymerizable monomer generally adopted in this invention comprises a photo-polymerizable monomer, a thermal-polymerizable monomer, or a combination thereof. For example (but not limited to), the polymerizable monomer may be selected from a group consisting of compounds with a formula (I) or (II):

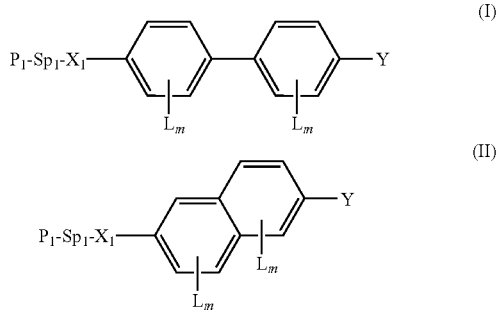

wherein, $P_1$ is independently a polymerizable group, for example acrylate or methacrylate;

$Sp_1$ is independently a spacer group, for example, a straight carbon chain with at least one carbon atom;

$X_1$ is independently —O—, —S—, —OCH$_2$—, —CO—, —COO—, —OCO—, —CO—NR—, —NR—CO—, —OCH$_2$—, —SCH$_2$—, —CH$_2$S—, —CH=CH—COO—, —OCC—CH=CH— or a single bond, wherein R is alkyl;

L is independently —F, —Cl, —CN, or alkyl, alkylcarbonyl, alkoxycarbonyl or alkylcarbonyloxy with 1 to 7 carbon atoms; and m is not less than 1; wherein one or more H atoms can be replaced by F or Cl atoms when L is alkyl, alkylcarbonyl, alkoxycarbonyl or alkylcarbonyloxy with 1 to 7 carbon atoms;

Y is independently —H, —F, —Cl, —CN, —SCN, —SF$_5$H, —NO$_2$, a single bond or a branched alkyl with 1 to 12 carbon atoms, or —X$_2$—Sp$_2$—P$_2$, wherein:

$P_2$ is independently a polymerizable group, for example acrylate or methacrylate;

$Sp_2$ is independently a spacer group, for example, a straight carbon chain with at least one carbon atom; and $X_2$ is independently —O—, —S—, —OCH$_2$—, —CO—, —COO—, —OCO—, —CO—NR—, —NR—CO—, —OCH$_2$—, —SCH$_2$—, —CH$_2$S—, —CH=CH—COO—, —OCC—CH=CH— or a single bond, wherein R is alkyl.

To let people skilled in this field can easily realize the LCD according to the embodiments of the present invention, an PSA LCD as an embodiment is described below with reference to the attached drawing in which like numerals identify like elements.

Figure 2:
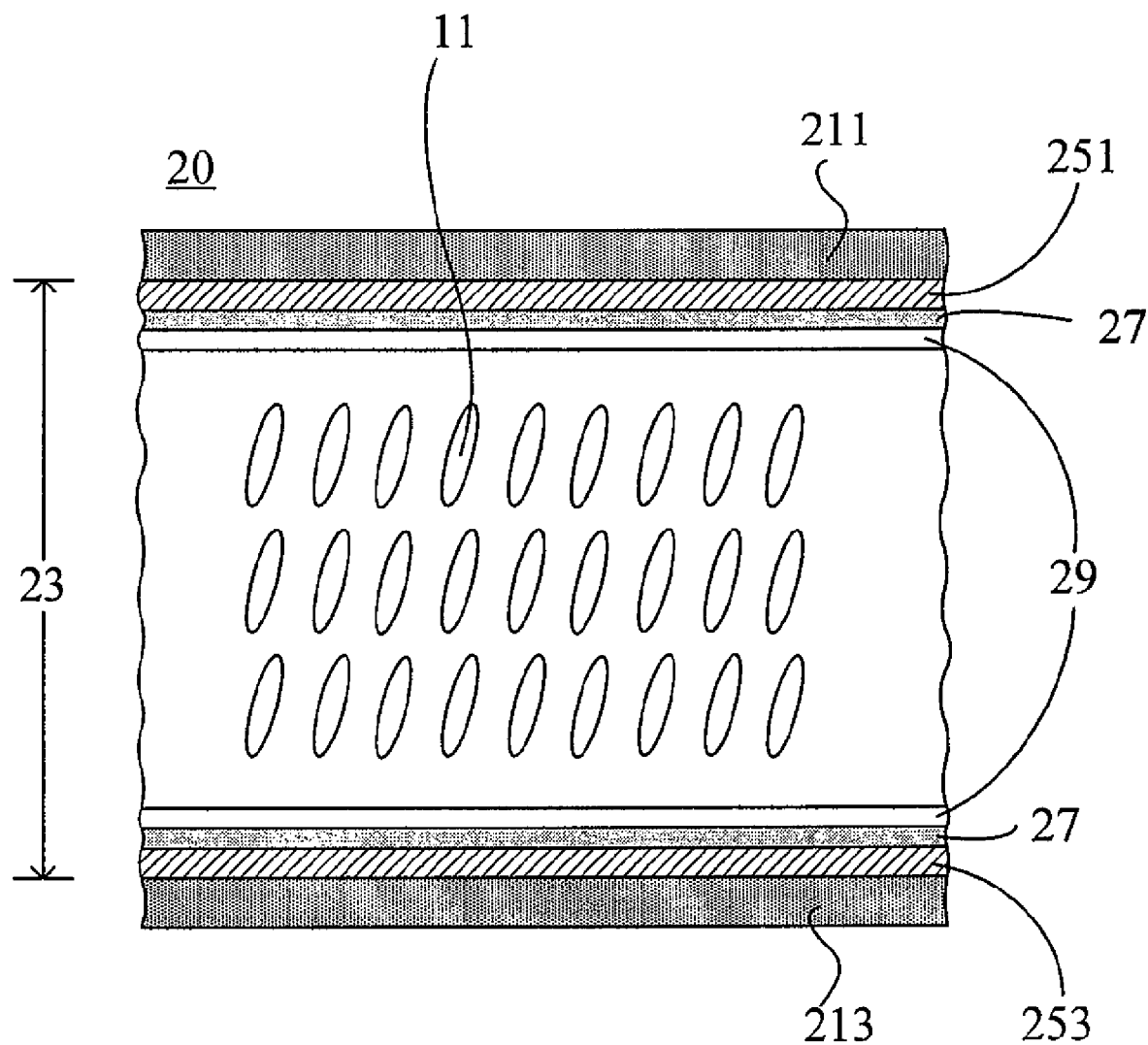
FIG. 2 depicts a schematic view of one LCD embodiment of this invention.

FIG. 2 illustrates a PSA LCD 20 in accordance with an embodiment of this invention. The LCD 20 comprises a first substrate 211, a second substrate 213, and a liquid crystal 11 according to the invention sealed therebetween. Additionally, a first electrode 251 and a second electrode 253 are provided respectively on the surfaces of the first substrate 211 and the second substrate 213 facing towards each other to provide an electric field for twisting the liquid crystal 11. As shown in FIG. 2, an alignment film 27 is also provided on the surfaces of the first electrode 251 and the second electrode 253 facing towards each other to direct the alignment of the liquid crystal 11. A polymer film 29 is provided on the surface of the alignment film 27 to assist the alignment of the liquid crystal 11. Also shown in FIG. 2, the two substrates are separated with a predetermined distance, i.e., a cell gap 23, which typically ranges from about 2.5 μm to about 10 μm.

Any suitable processes can be used in the manufacture of the LCD of the subject invention, such as color filter fabrication process, thin-film transistor array process, liquid crystal cell process, and module assembly process. All the aforementioned processes are well known in this technical field and thus their details will not be further described herein. In the case of a PSA LCD, the polymer film disposed on the alignment film can be provided by injecting or dropping a liquid crystal material combination containing, in addition to a liquid crystal of this invention, a polymerizable monomer into the cell of the LCD, and then polymerizing the polymerizable monomer so as to form the polymer film on the alignment film.

Thus, the subject invention further relates to a liquid crystal material combination comprising a liquid crystal of this invention and a polymerizable monomer as mentioned above. According to this invention, the amount of the polymerizable monomer may be determined by those of ordinary skill in the art depending on the actual requirements. In general, the amount of the polymerizable monomer ranges from about 0.01 wt % to about 5 wt % based on the weight of the liquid crystal.

The following examples are provided to further illustrate this invention to give those of ordinary skill in the art a more clear understanding of the advantages and technical features of this invention.

EXAMPLE 1

A simulation of the transmittance was conducted by use of liquid crystal materials 1 to 5 respectively in a vertical alignment LCD to observe the influences of the splay elastic constant ($K_{11}$), the torsion elastic constant ($K_{22}$), the bend elastic constant ($K_{33}$), the dielectric anisotropy ($\Delta\in$) and the viscosity coefficient ($\gamma$) on the transmittance, with the results shown in Table 1.

TABLE 1

| | Liquid crystal material | | | | |
|---|---|---|---|---|---|
| | 1 | 2 | 3 | 4 | 5 |
| $K_{11}$ and $K_{33}$ ($10^{-11}$ N) | 1.5 | 1.1 | 1.5 | 1.5 | 1.5 |
| $K_{22}$ ($10^{-11}$ N) | 0.8 | 0.8 | 0.8 | 0.8 | 0.5 |
| $\gamma$ (P) | 0.11 | 0.11 | 0.11 | 0.14 | 0.11 |
| $\Delta\in$ | −3 | −3 | −3.5 | −3.5 | −3 |
| Transmittance at a 7 V voltage (%) | 24.1 | 23.9 | 24.1 | 24.0 | 24.0 |
| Transmittance at a 4.2 V voltage (%) | 18.1 | 24.6 | 21.6 | 21.6 | 18.1 |

Table 1 reveals that, as compared to $K_{22}$ and $\gamma$, $K_{11}$, $K_{33}$ and $\Delta\in$ may better reflect the transmittance of the liquid crystal materials. In more detail, it can be seen from the results corresponding to the liquid crystal materials 1 and 5 that when $K_{11}$, $K_{33}$, $\gamma$ and $\Delta\in$ are fixed, the liquid crystal materials 1 and 5 with different $K_{22}$ values (0.8 and 0.5 respectively) exhibit no substantial difference in the transmittance (24.1% and 24.0% respectively at a 7 V voltage; and both being 18.1% at a 4.2 V voltage). Similarly, it can be seen from the results corresponding to the liquid crystal materials 3 and 4 that when $K_{11}$, $K_{22}$, $K_{33}$ and $\Delta\varepsilon$ are fixed, the liquid crystal materials 3 and 4 with different γ values (0.11 and 0.14 respectively) exhibit no substantial difference in the transmittance (24.1% and 24.0% respectively at a 7 V voltage; and both being 21.6% at a 4.2 V voltage). In contrast, it can be seen by comparison between the liquid crystal materials 1 and 2 that when $K_{22}$, γ and $\Delta\varepsilon$ are fixed, and at the low driving voltage (e.g., 4.2 V), the liquid crystal materials 1 and 2 with different $K_{11}$ and $K_{33}$ values exhibit a significant difference in transmittance, 18.1% and 24.6% respectively, which means that the liquid crystal 2 has a better performance in terms of transmittance. Additionally, it can be seen by comparison between the liquid crystal materials 1 and 3 that when $K_{11}$, $K_{33}$, $K_{22}$, and γ are fixed, and at the low driving voltage (e.g., 4.2 V), the liquid crystal materials 1 and 2 with different $\Delta\varepsilon$ values (−3 and −3.5 respectively) exhibit a significant difference in transmittance, 18.1% and 21.6% respectively, which means that the liquid crystal 3 has a better performance in terms of transmittance.

It can be seen from Example 1 that when the liquid crystal parameters $K_{22}$, γ and $\Delta\varepsilon$ are fixed, the parameters $K_{11}$ and $K_{33}$ will influence the transmittance of the liquid crystal materials. On the other hand, when $K_{11}$, $K_{33}$, $K_{22}$, and γ are fixed, the parameter $\Delta\varepsilon$ will influence the transmittance of the liquid crystal materials.

EXAMPLE 2

A test was made on the LCD with a structure depicted in FIG. 2, in which a variation is made only to the liquid crystal 11 and other elements still remain unchanged.

Initially, the liquid crystal material 1 with the following parameters was adopted for the liquid crystal 11: $\Delta\varepsilon=-3$, $K_{11}=1.52\times10^{-11}$ N, $K_{33}=1.55\times10^{-11}$ N, and then a transmittance measurement instrument was used to make optical measurements on the assembled LCD, with the measurement results shown in Table 2 (LC 1).

Then, the liquid crystal material 2 with the following parameters was adopted instead for the liquid crystal 11: $\Delta\varepsilon=-3$, $K_{11}=1.37\times10^{-11}$ N, $K_{33}=1.41\times10^{-11}$ N, and subsequently a transmittance measurement instrument was used to make optical measurements on the assembled LCD, with the measurement results shown in Table 2 (LC 2).

Next, the liquid crystal material 3 with the following parameters was adopted instead for the liquid crystal 11: $\Delta\varepsilon=-3.5$, $K_{11}=1.52\times10^{-11}$ N, $K_{33}=1.5\times10^{-11}$ N, and subsequently a transmittance measurement instrument was used to make optical measurement on the assembled LCD, with the measurement results shown in Table 2 (LC 3).

TABLE 2

|  | LC | | |
| --- | --- | --- | --- |
|  | LC 1 | LC 2 | LC 3 |
| $\Delta\varepsilon$ | −3 | −3 | −3.5 |
| $K_{11}$ | 15.2 | 13.7 | 15.2 |
| $K_{33}$ | 15.5 | 14.1 | 15 |
| T (%) | 3.70 | 3.90 | 4.40 |

As shown in Table 2, it can be seen by comparison between the liquid crystal materials 1 and 2 that when $\Delta\varepsilon$ is fixed, the liquid crystal material 2, with $K_{11}$ and $K_{33}$ values of 13.7 and 14.1 respectively, exhibits a better transmittance (%) than the liquid crystal material 1 with $K_{11}$ and $K_{33}$ values of 15.2 and 15.5 respectively, i.e., the liquid crystal material 2 has a transmittance value (%) of 3.9, while the liquid crystal material 1 has a transmittance value (%) of 3.7. Similarly, it can be seen by comparison between the liquid crystal materials 1 and 3 that when $K_{11}$, is fixed, the liquid crystal material 1 with $\Delta\varepsilon$ and $K_{33}$ values of −3.5 and 15 respectively exhibits a better transmittance (%) than the liquid crystal material 3 with $\Delta\varepsilon$ and $K_{33}$ values of −3 and 15.5 respectively, i.e., the liquid crystal material 3 has a transmittance value (%) of 4.4, while the liquid crystal material 1 has a transmittance value (%) of 3.7.

It can be seen from Example 2 that by selecting a liquid crystal material with suitable $\Delta\varepsilon$, $K_{11}$, and $K_{33}$ values, the transmittance of the LCD can be effectively improved.

The above disclosure is related to the detailed technical contents of this invention and the inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A liquid crystal display, comprising:
   a first substrate (211);
   a second substrate (213); and
   a plurality of liquid crystal molecules (11) sealed between the first substrate (211) and the second substrate (213), having following properties:
   (i) a dielectric anisotropy ($\Delta\varepsilon$) ranging from about −2.5 to about −5;
   (ii) a splay elastic constant ($K_{11}$) ranging from about $1.1\times10^{-11}$ N to about $1.6\times10^{-11}$ N;
   (iii) a bend elastic constant ($K_{33}$) ranging from about $1.1\times10^{-11}$ N to about $1.6\times10^{-11}$ N; and
   (iv) a relationship among $\Delta\varepsilon$, $K_{11}$(N) and $K_{33}$(N) being as follows:

$$\frac{K_{11}+K_{33}}{|10\times\Delta\varepsilon|} < 1.28\times10^{-12}.$$

2. The liquid crystal display according to claim 1, wherein $\Delta\varepsilon$ ranges from about −3 to about −3.5 and each of $K_{11}$ and $K_{33}$ independently ranges from about $1.1\times10^{-11}$ N to about $1.55\times10^{-11}$ N.

3. The liquid crystal display according to claim 1, wherein $\Delta\varepsilon$ ranges from about −3.0 to about −5.

4. The liquid crystal display according to claim 1, wherein $K_{11}$ ranges from about $1.37\times10^{-11}$ N to about $1.6\times10^{-11}$ N.

5. The liquid crystal display according to claim 1, wherein $K_{33}$ ranges from about $1.37\times10^{-11}$ N to about $1.6\times10^{-11}$ N.

6. The liquid crystal display according to claim 1, further comprising:
   a first electrode (251) and a second electrode (253), respectively disposed on the surfaces of the first substrate (211) and the second substrate (213) which are opposite to each other; and
   at least one alignment film (27) on the first electrode (251) and/or the second electrode (253).

7. The liquid crystal display according to claim 6, further comprising a polymer film (29) on the alignment film (27).

8. The liquid crystal display according to claim 1, wherein a predetermined cell gap (23) ranging from about 2.5 μm to about 10 μm is present between the first substrate (211) and the second substrate (213).

9. A liquid crystal, having following properties:
(i) a dielectric anisotropy ($\Delta \in$) ranging from about −2.5 to about −5;
(ii) a splay elastic constant ($K_{11}$) ranging from about $1.1 \times 10^{-11}$ N to about $1.6 \times 10^{-11}$ N;
(iii) a bend elastic constant ($K_{33}$) ranging from about $1.1 \times 10^{-11}$ N to about $1.6 \times 10^{-11}$ N; and
(iv) a relationship among $\Delta \in$, $K_{11}(N)$ and $K_{33}(N)$ being as follows:

$$\frac{K_{11}+K_{33}}{|10 \times \Delta \varepsilon|} < 1.28 \times 10^{-12}.$$

10. The liquid crystal according to claim 9, which is a negative liquid crystal and comprises a compound with a formula (III), (IV), (V) or (VI):

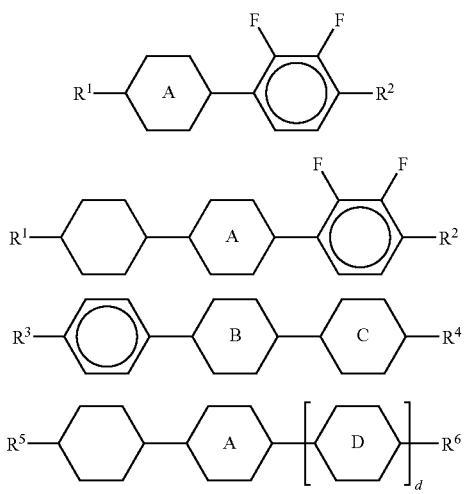

wherein,
$R^1$, $R^2$, $R^3$, $R^4$ and $R^6$ are independently alkyl with 1 to 12 carbon atoms, wherein one CH$_2$ group or two CH$_2$ groups that are not adjacent to each other can be replaced by —O—, —CH=CH—, —CO—, —OCO— or —COO—;
$R^5$ is alkenyl with 2 to 8 carbon atoms;
d is 0 or 1;

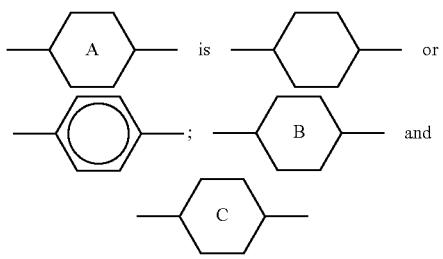

are independently

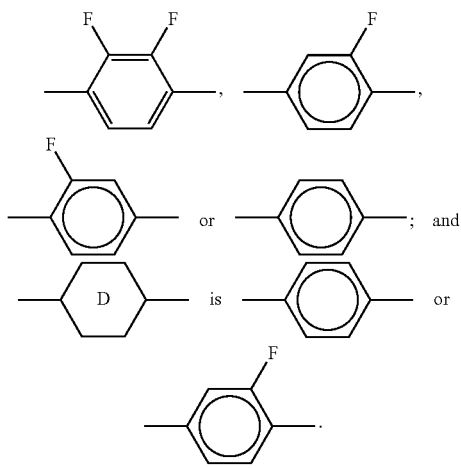

11. The liquid crystal according to claim 9, wherein $\Delta \in$ ranges from about −3 to about −3.5 and each of $K_{11}$, and $K_{33}$ independently ranges from about $1.1 \times 10^{-11}$ N to about $1.55 \times 10^{-11}$ N.

12. The liquid crystal according to claim 9, wherein $\Delta \in$ ranges from about −3.0 to about −5.

13. The liquid crystal according to claim 9, wherein $K_{11}$ ranges from about $1.37 \times 10^{-11}$ N to about $1.6 \times 10^{-11}$ N.

14. The liquid crystal according to claim 9, wherein $K_{33}$ ranges from about $1.37 \times^{-11}$ N to about $1.6 \times 10^{-11}$ N.

15. A liquid crystal material combination, comprising a liquid crystal and a polymerizable monomer, wherein the liquid crystal has following properties:
(i) a dielectric anisotropy ($\Delta \in$) ranging from about −2.5 to about −5;
(ii) a splay elastic constant ($K_{11}$) ranging from about $1.1 \times 10^{-11}$ N to about $1.6 \times 10^{-11}$ N;
(iii) a bend elastic constant ($K_{33}$) ranging from about $1.1 \times 10^{-11}$ N to about $1.6 \times 10^{-11}$ N; and
(iv) a relationship among $\Delta \in$, $K_{11}(N)$ and $K_{33}(N)$ being as follows:

$$\frac{K_{11}+K_{33}}{|10 \times \Delta \varepsilon|} < 1.28 \times 10^{-12}.$$

16. The liquid crystal material combination according to claim 15, wherein the polymerizable monomer comprises a photo-polymerizable monomer, a thermal-polymerizable monomer, or a combination thereof.

17. The liquid crystal material combination according to claim 16, wherein the polymerizable monomer comprises a compound with a formula (I) or (II):

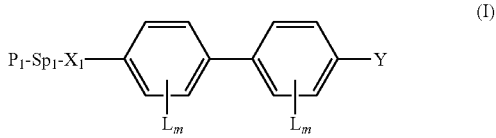

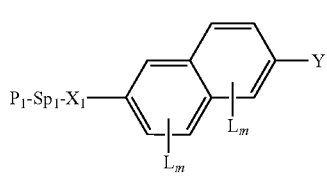

(II)

wherein,
P₁ is independently acrylate or methacrylate;
Sp₁ is independently a straight carbon chain with at least one carbon atom;
$X_1$ is independently —O—, —S—, —OCH₂—, —CO—, —COO—, —OCO—, —CO—NR—, —NR—CO—, —OCH₂—, —SCH₂—, —CH₂S—, —CH=CH—COO—, —OCC—CH=CH— a single bond, wherein R is alkyl;
L is independently —F, —Cl, —CN, or alkyl, alkylcarbonyl, alkoxycarbonyl or alkylcarbonyloxy with 1 to 7 carbon atoms; and m is not less than 1; wherein one or more H atoms can be replaced by F or Cl atoms as L is alkyl, alkylcarbonyl, alkoxycarbonyl or alkylcarbonyloxy with 1 to 7 carbon atoms;
Y is independently —H, —F, —Cl, —CN, —SCN, —SF₅H, —NO₂, alkyl with 1 to 12 carbon atoms, or —X₂—Sp₂—P₂, wherein:
P₂ is independently acrylate or methacrylate;
Sp₂ is independently a straight carbon chain with at least one carbon atom;
$X_2$ is independently —O—, —S—, —OCH₂—, —CO—, —COO—, —OCO—, —CO—NR—, —NR—CO—, —OCH₂—, —SCH₂—, —CH₂S—, —CH=CH—COO—, —OCC—CH=CH— or a single bond, wherein R is alkyl.

18. The liquid crystal material combination according to claim 15, wherein the liquid crystal is a negative liquid crystal and comprises a compound with a formula (III), (IV), (V) or (VI):

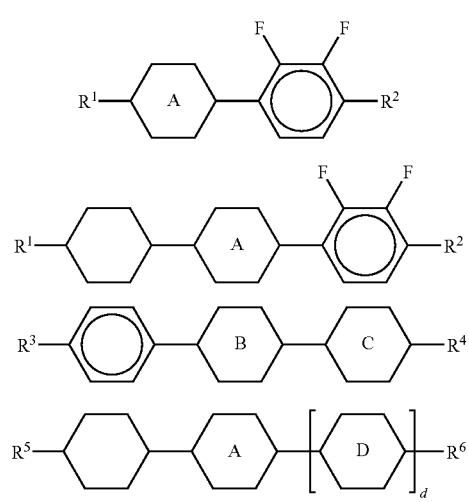

wherein,
$R^1, R^2, R^3, R^4$ and $R^6$ are independently alkyl with 1 to 12 carbon atoms, wherein one CH₂ group or two CH₂ groups that are not adjacent to each other can be replaced by —O—, —CH=CH—, —CO—, —OCO— or —COO—;
$R^5$ is alkenyl with 2 to 8 carbon atoms;
d is 0 or 1;

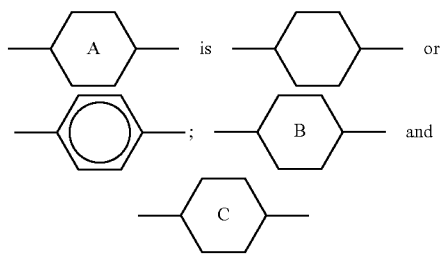

are independently

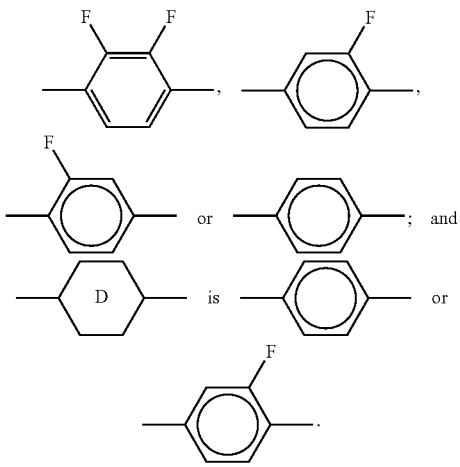

19. The liquid crystal material combination according to claim 15, wherein the amount of the polymerizable monomer ranges from about 0.01 wt % to about 5 wt % based on the weight of the liquid crystal.

20. The liquid crystal material combination according to claim 15, wherein $\Delta\epsilon$ ranges from about −3 to about −3.5 and each of $K_{11}$ and $K_{33}$ independently ranges from about $1.1 \times 10^{-11}$ N to about $1.55 \times 10^{-11}$ N.

21. The liquid crystal material combination according to claim 15, wherein $\Delta\epsilon$ ranges from about −3.0 to about −5.

22. The liquid crystal material combination according to claim 15, wherein $K_{11}$ ranges from about $1.37 \times 10^{-11}$ N to about $1.6 \times 10^{-11}$ N.

23. The liquid crystal material combination according to claim 15, wherein $K_{33}$ ranges from about $1.37 \times 10^{-11}$ N to about $1.6 \times 10^{-11}$ N.

* * * * *